United States Patent [19]

Solomon

[11] Patent Number: 4,474,309

[45] Date of Patent: Oct. 2, 1984

[54] STEPPING MOTOR CONTROL PROCEDURE FOR ACHIEVING VARIABLE RATE, QUASI-CONTINUOUS FLUID INFUSION

[75] Inventor: Edward G. Solomon, Menlo Park, Calif.

[73] Assignee: OXIMETRIX, Inc., Mountain View, Calif.

[21] Appl. No.: 314,038

[22] Filed: Oct. 22, 1981

[51] Int. Cl.³ .............................................. A61M 5/14
[52] U.S. Cl. ......................................... 222/1; 222/63; 318/685; 412/22; 604/67; 604/152
[58] Field of Search ............... 222/1, 333, 63; 604/67, 604/152; 417/12, 22; 318/685

[56] References Cited

U.S. PATENT DOCUMENTS

| | | | |
|---|---|---|---|
| 3,985,133 | 10/1976 | Jenkins et al. | 604/67 |
| 4,137,913 | 2/1979 | Georgi | 222/63 X |
| 4,352,656 | 10/1982 | Patterson | 417/22 |
| 4,396,385 | 8/1983 | Kelly et al. | 604/152 |

*Primary Examiner*—Joseph J. Rolla
*Assistant Examiner*—Frederick R. Handren
*Attorney, Agent, or Firm*—Robert S. Kelly

[57] ABSTRACT

A control procedure for governing the incremental step operation of a pump stepping motor (74) employed in conjunction with a parenteral fluid metering device (2) is disclosed. The control procedure enables fluid to be pumped from the metering device (2) in non-pulsatile, essentially continuous fashion by suitably adjusting the stepping motor speed to compensate for the interruption of fluid flow which occurs during the refill phase ($P_R$) of each pumping cycle (C). Adjustment of the stepping motor speed also compensates for non-linearities otherwise introduced into the fluid flow as a result of the camming mechanism (76,78) utilized to convert rotary stepping motor movement into rectilinear pumping movement. Operating power for the stepping motor is conserved by drawing relatively large amounts of current through the stepping motor (74) only at the outset of each incremental step while drawing relatively smaller amounts of current through the stepping motor (74) during the remaining interval between incremental steps.

4 Claims, 8 Drawing Figures

STEPPING MOTOR CONTROL PROCEDURE FOR ACHIEVING VARIABLE RATE, QUASI-CONTINUOUS FLUID INFUSION

TECHNICAL FIELD

The present invention is directed to a means and method for administering fluids to patients intravenously or intraarterially and more particularly concerns a mechanism and a control procedure such that carefully metered portions of fluid are delivered in quasi-continuous fashion to patients.

BACKGROUND ART

Considerable attention has been focused in recent years on intravenous and intraarterial delivery of fluids to patients. Precision control over the rate at which such parenteral delivery occurs is of critical importance, inasmuch as improper administration of fluids can retard the recovery of patients or, in extreme situations, lead to further injury or even death. Early parenteral delivery systems relied on gravity flow to transfer fluid from a fluid container or reservoir to the patient. Attempts to accurately regulate gravity flow, however, proved difficult because the pressure forcing the fluid between the reservoir and the patient decreased as the fluid level within the reservoir dropped during the delivery operation. Thus, delivery rates in gravity-flow systems tended to vary in an unacceptable manner.

More recent parenteral delivery systems have employed pump motors in an effort to increase fluid delivery rate accuracy. Often, the pump motors comprise stepping motors which drive plunger or piston-like fluid pumps in response to suitable stepping motor control procedures. These procedures are highly compatible with the precision control requirements of parenteral administration because they provide the necessary degree of accuracy and are capable of implementation through reliable and efficient microprocessor programming techniques. U.S. Pat. No. 4,037,598 issued to Georgi on Jul. 26, 1977; U.S. Pat. No. 3,994,294 issued to Knute on Nov. 30, 1976; U.S. Pat. No. 3,985,133 issued to Jenkins et al on Oct. 12, 1976 and U.S. Pat. No. 3,736,930 issued to Georgi on Jun. 5, 1973 all disclose intravenous delivery systems wherein stepping motors are utilized in conjunction with camming mechanisms and pumping structures to achieve accurate delivery rate control. In spite of the advantages offered by prior art systems, however, certain improvements in the fluid delivery characteristics of existing delivery systems can be made. For example, none of the stepping motor control procedures associated with the stepping motors of the aforementioned patents compensate for non-linearities introduced into the fluid delivery rate as a result of interaction between the camming mechanisms, the stepping motors, and the pumping structures. Nor are efforts made to minimize the pulsatile discontinuities in fluid flow brought about by the interruption of fluid delivery during those portions of each pumping cycle devoted to refilling the pumping structures. Consequently, the prior art fails to provide a parenteral administration system capable of pumping precise amounts of fluid at linear rates in essentailly continuous fashion.

SUMMARY OF THE INVENTION

It is therefore the object of the present invention to provide a control procedure for governing the operation of a pump motor in a parenteral fluid delivery system.

It is another object of the present invention to provide a motor control procedure for use with a parenteral fluid pump motor and camming mechnism wherein essentially linear fluid delivery rates are achieved despite the nonlinearities inherent in the conversion of rotary motor movement to rectilinear pumping movement.

It is yet another object of the present invention to provide a pump motor control procedure for use with a parenteral fluid pump motor and camming mechanism wherein the speed of the motor is varied in accordance with the angular position of the camming mechanism in order to compensate for non-linearities which occur in the conversion of rotary motor movement to rectilinear pumping movement.

The foregoing objects are achieved by providing a pump controller mechanism that includes a stepping motor connected to a plunger through a camming means with the camming means driving the plunger through a plurality of rectilinear distances as the motor rotates the camming means through a plurality of equiangular distances. The rectilinear distances at the ends of the pumping stroke are shorter than those at the center of the stroke, and hence a control means is provided to drive the motor at a higher rate at the ends of the stroke to accommodate this and achieve a generally uniform flow.

In another aspect of the present invention, the time required for refilling the pumping chamber is also taken into account by initially driving the stepping motor at a high rate for a time sufficient to make up the time required for filling so that the motor can return to the preset rate which is the desired delivery rate for the entire pumping cycle.

BRIEF DESCRIPTION OF THE DRAWINGS

These and other objects of the present invention can best be understood by examining the following Brief Description Of The Drawings and Best Mode For Carrying Out The Invention, in which.

BEST MODE FOR CARRYING OUT THE INVENTION

Figure 1:
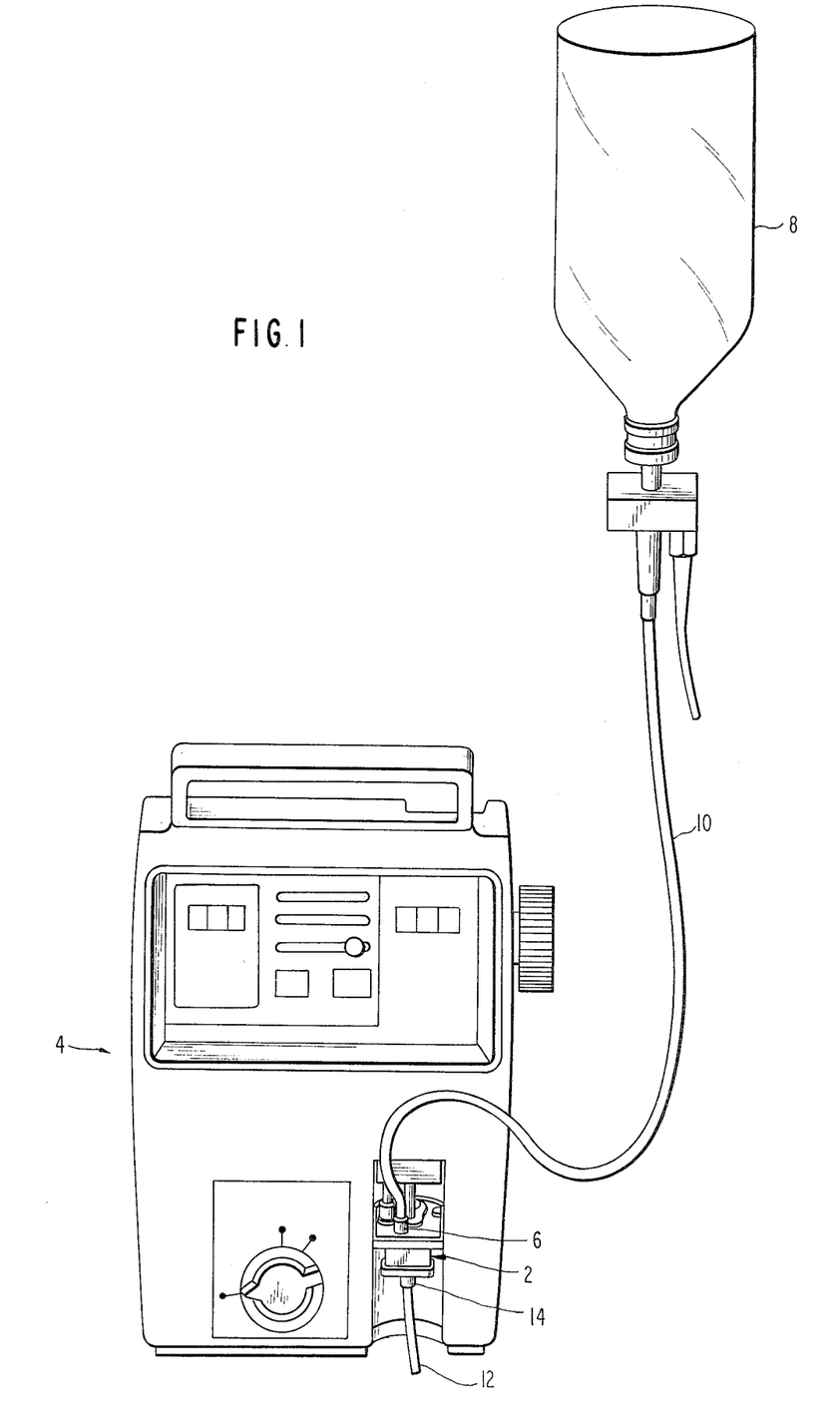
FIG. 1 is a perspective view illustrating the parenteral delivery system of the present invention.
Figure 2:
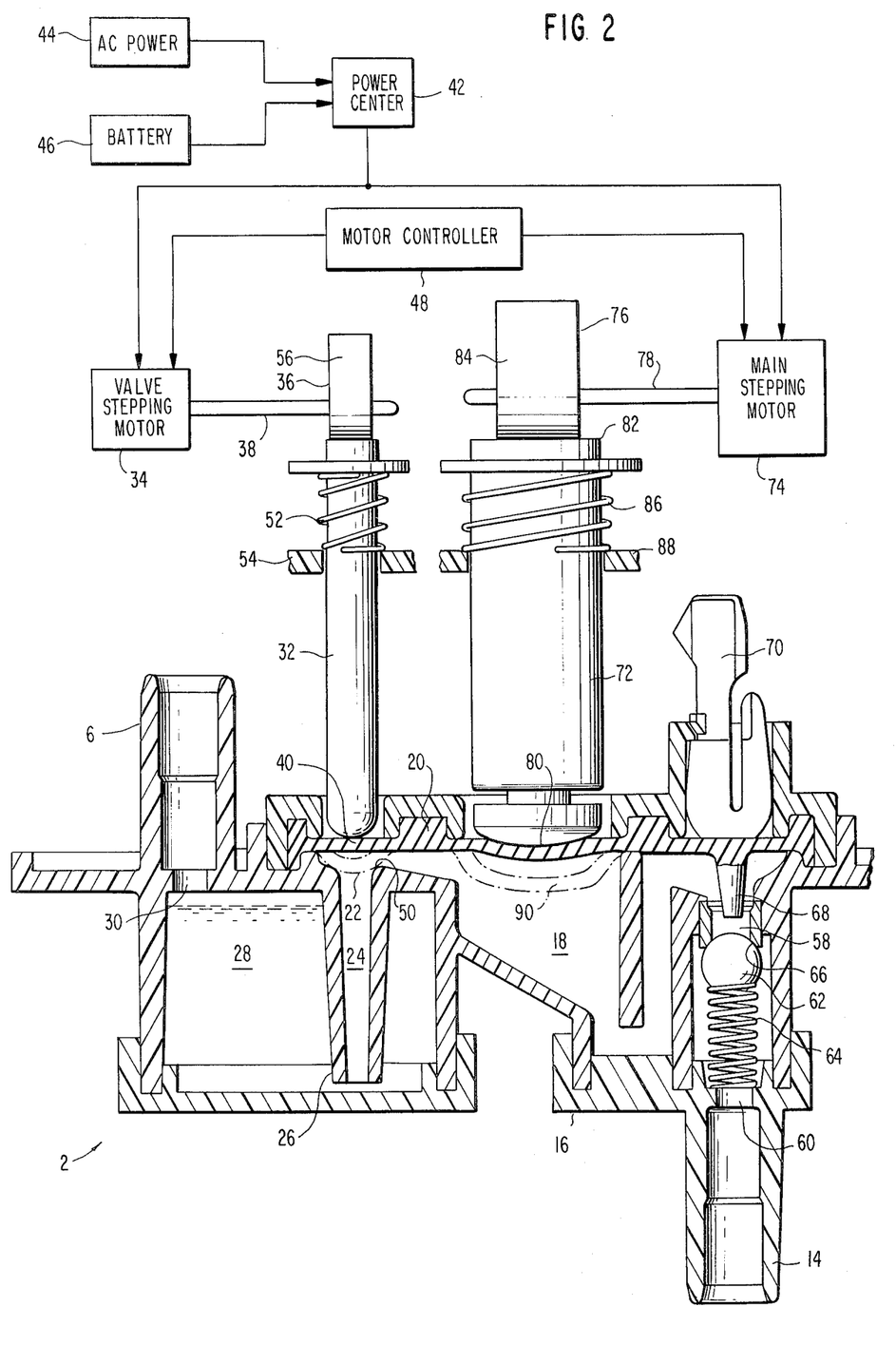
FIG. 2 is a cross-sectional view of the pumping cassette, valve stepping motor and main stepping motor employed in the parenteral delivery system of FIG. 1.

One type of parenteral fluid metering device for delivering controlled amounts of fluid to a patient is schematically illustrated in FIGS. 1 and 2. Basic and improved embodiments of the fluid metering device are disclosed in co-pending application Ser. Nos. 174,666 now U.S. Pat. No. 4,336,800 and 278,954; respectively filed on Aug. 1, 1980 and Jun. 30, 1981. Both of these co-pending applications are assigned to the assignee of the present invention and both are incorporated herein by reference. For the sake of convenience, only the improved fluid metering device of application Ser. No. 278,954 will be described in any detail, although it is understood that the control procedure of the present invention can be suitably modified for use with the fluid metering device of application Ser. No. 174,666. Referring first to FIG. 1, the fluid metering device 2 is shown positioned within a metering device control unit 4. An in-flow conduit 6 on fluid metering device 2 is connected to a container of fluid 8 by means of conventional tubing 10. Tubing 12, extending from out-flow conduit 14 of the fluid metering device 2, transfers precise amounts of fluid to the patient being treated in response to actuation of a stepping motor and camming mechanism (not shown in FIG. 1) housed in control unit 4.

Turning to FIG. 2, the construction of the fluid metering device 2, as well as the stepping motor and camming mechanism, is shown in greater detail. Fluid metering device 2 includes a hollow cassette structure 16 having a pumping chamber 18 disposed therein. A resilient diaphragm 20 is secured across the top of pumping chamber 18. An inlet port 22 at one end of passageway 24 formed in gas retention conduit 26 permits fluid to pass from a gas retention chamber 28 into pumping chamber 18. Gas retention chamber 28 in turn fluidically communicates with in-flow conduit 6 through an intermediate passageway 30. A valve actuator 32 operatively connected to valve stepping motor 34 via a cam and shaft mechanism 36, 38 controls the admission of fluid into pumping chamber 18 by displacing a portion 40 of resilient diaphragm 20 positioned above inlet port 22. Current is supplied to valve stepping motor 34 by a power control center 42 which may be alternately connected to an AC power supply 44 or a battery supply 46. Valve stepping motor 34 is driven through a series of incremental steps in response to commands received from motor controller 48, whereupon valve actuator 32 reciprocates to move the diaphragm portion 40 between an open position, as indicated by solid lines in FIG. 2, and a sealing engagement with a valve seat 50 formed around the periphery of inlet port 22, as indicated in phantom in FIG. 2. A biasing means such as spring 52 seated on hollow boss 54 formed in control unit 4 provides the necessary force for urging valve actuator 32 into positive contact with the camming surface 56 of cam 36.

An outlet port 58 is formed in pumping chamber 18 opposite inlet port 22. Outlet port 58 communicates with outlet conduit 14 through an intermediate passageway 60. A ball check 62 is mounted between outlet port 58 and intermediate passageway 60. A biasing means such as spring 64 urges the ball check into sealing engagement with a valve seat 66 formed around the periphery of outlet port 58. A projection 68 formed on resilient diaphragm 20 opposite ball check 64 displaces the ball check from valve seat 66 during pump priming operations. A manual latch valve 70 is used to move projection 68 into contact with the ball check.

Motive power for pumping fluid through the cassette 16 of fluid metering device 2 is supplied by a plunger 72 operatively connected to a main stepping motor 74 via a cam and shaft mechanism 76, 78. Main stepping motor 74 also receives current from power control center 42 under the command of motor controller 48. One end 80 of plunger 72 contacts resilient diaphragm 20 while the remaining end 82 is urged into positive contact with the camming surface 84 of cam 76 by a biasing means such as spring 86 seated on hollow boss 88 of control unit 4. The incremental or step rotation of main stepping motor 74, and hence of cam 76, drives plunger 72 in a reciprocal fashion between a fully retracted position, indicated by solid lines in FIG. 2, and a fully extended position indicated in phantom at 90 in FIG. 2. Resilient diaphragm 20 flexes in response to the reciprocal motion of plunger 72 to periodically vary the volume of pumping chamber 18, thereby providing the pumping action necessary to drive a metered amount of fluid from the pumping chamber into the fluid outflow conduit 14.

Figure 3:
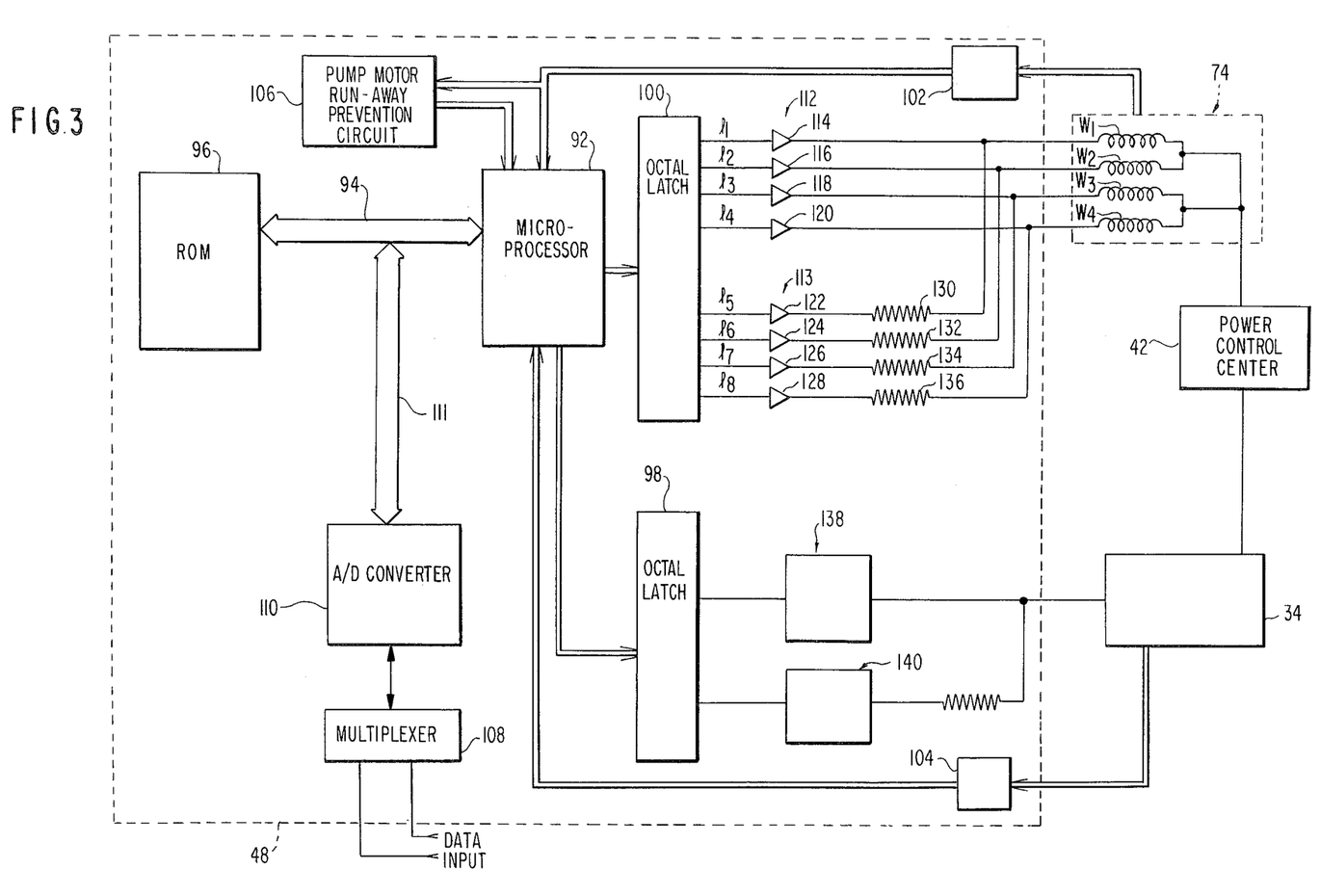
FIG. 3 schematically depicts a motor controller for governing the operation of the valve stepping motor and main stepping motor of FIG. 2, whereby the amount of current drawn through both the valve stepping motor and main stepping motor is alternately switched between high and low values in order to conserve energy.

The motor controller 48 which governs the operation of valve stepping motor 34 and main stepping motor 74 is schematically illustrated in FIG. 3. Motor controller 48 includes a microprocessor 92 connected by a data link 94 to a read-only-memory 96. Suitable control procedures for the valve stepping motor 34 and the main stepping motor 74 are stored in read-only-memory 96 and supplied to microprocessor 92 on demand. The microprocessor in turn directs a pair of octal latches 98, 100 to drive the valve stepping motor and the main stepping motor respectively through their incremental steps in accordance with the control procedures stored in the read-only-memory. Sensing means 102 and 104 provide a count of the number of steps taken by the valve stepping motor and the main stepping motor, enabling microprocessor 92 to determine the incremental step position of each. Pump run-away prevention circuit 106 is connected to sensing means 102 and monitors the speed of main stepping motor 74 to prevent the occurance of potentially dangerous fluid over- or under-delivery conditions, as disclosed more fully in co-pending application Ser. No. 320,528, filed Nov. 12,1981 and incorporated herein by reference. Finally, multiplexer 108 is connected to various data sensors such as the plunger pressure transducer (not shown) disclosed in aforementioned Ser. No. 278,954. A/D converter 110 converts the signals from multiplexer 108 into a form useable by microprocessor 92, feeding the signals so converted to the microprocessor via data link 111.

Octal latch 100, under the direction of microprocessor 92 in FIG. 3, is connected to high and low current drivers 112, 113 via leads $l_1$–$l_8$. The high current drivers 112 comprise a set of transistor drivers 114, 116, 118 and 120 respectively connected in series with the motor windings $W_1$, $W_2$, $W_3$ and $W_4$ of main stepping motor 74. The low current drivers 113 comprise a similar set of transistor drivers 122, 124, 126 and 128 respectively connected in series with windings $W_1$–$W_4$ through a set of resistors 130, 132, 134 and 136. For each incremental step taken by main stepping motor 74, octal latch 100 generates a combination of control signals along leads $l_1$, $l_2$, $l_3$ and $l_4$ to switch high current drivers 114–120 on. Thereafter, a relatively large current is drawn from the power control center 42 through the main stepping motor windings $W_1$–$W_4$ and drivers 114–120 to provide sufficient energy for rotating the main stepping motor from one incremental step position to the next. It should here be noted that the energy required by main stepping motor 74 in effecting the downward stroke of plunger 72 (not shown in FIG. 3) is not constant throughout each incremental step of the main stepping motor, but rather varies as a function of the elastic characteristics of resilient diaphragm 20 (also not shown in FIG. 3). That is, during the interval between each incremental step, the resilient diaphragm attempts to return to its original or undeformed position, and in so doing exerts a force against plunger 72 tending to move the plunger back to a retracted position. At the beginning of the next incremental step, a relatively greater amount of energy must be expended to overcome the force exerted by the diaphragm before plunger 72 can continue its downward movement. Once an incremental step has been completed, main stepping motor 74 again moves into a holding or "quiescent" mode and less energy is required to maintain the plunger and diaphragm at the displaced position associated with that incremental step.

The circuitry of FIG. 3 compensates for the differing energy requirements of the main stepping motor holding mode and the main stepping motor stepping mode by adjusting the current drawn through the main stepping motor between steps, using the set of low current drivers 122, 124, 126 and 128 connected in series with main stepping motor windings $W_1$–$W_4$ through the set of resistors 130, 132, 134 and 136. A short time after the main stepping motor rotates to its next incremental step position in response to the switching on of high current drivers 114–120, octal latch 100 turns the high current drivers off while simultaneously supplying a combination of control signals along leads $l_5$, $l_6$, $l_7$ and $l_8$ to turn low current drivers 122–128 on. Current is subsequently drawn from power control center 42 through windings $W_1$–$W_4$ and continues to pass through resistors 130–136 to the low current drivers. The presence of resistors 130–136, of course, reduces the amount of current drawn from power control center 42 to a level sufficient to meet the requirements of main stepping motor 74 during the main stepping motor holding mode. Thus, the net amount of energy expended in operating main stepping motor 74 is conserved. Where high incremental step rates occur, such as where high fluid delivery rates have been selected, it is possible for the interval between incremental steps to be shorter than the pre-programmed switching interval between the main stepping motor stepping and holding modes. In the latter case, octal latch 100 never has the opportunity to switch the low current drivers on and the main stepping motor will not draw any low holding current between its incremental steps.

An analogous arrangement of high current drivers and low current drivers, shown generally at 138 and 140 in FIG. 3, are controlled by octal latch 98 to energize valve stepping motor 34 and drive valve actuator 32 against portion 40 of resilient diaphragm 20. The smaller size of the valve stepping motor relative to main stepping motor 74 permits the overall current level in both the stepping and the holding modes of the valve stepping motor to be reduced.

The pumping operation of fluid metering device 2 will now be described. Returning to FIG. 2, it can be seen that incoming fluid transmitted by tubing 10 to fluid in-flow conduit 6 passes into gas retention chamber 28, whereupon any gases otherwise present in the fluid are prevented from reaching pumping chamber 18 by the presence of gas retention conduit 26. Liquid free of gas bubbles next travels from the gas retention chamber 28 through passageway 24 to inlet port 22. During the refill phase of each pumping cycle, valve stepping motor 34 operates to reciprocate valve actuator 32 upwardly, allowing fluid free of gas bubbles to pass through the inlet port into pumping chamber 18. Shortly thereafter, plunger 72 is reciprocated upwardly by main stepping motor 74 to increase the volume and reduce the pressure within pumping chamber 18, aiding the flow of fluid through the inlet port. The spring-loaded ball check 62 seated against valve seat 66 effectively closes off outlet port 58 while valve actuator 32 is in the open position. Accordingly, no fluid can leak into fluid out-flow conduit 14 during the refill phase of the pumping cycle and precise control over the amount of fluid to be pumped from pumping chamber 18 is maintained. After a brief interval in the open position, valve actuator 32 is moved to a closed position. Plunger 72 is then reciprocated downwardly as described hereinabove to decrease the volume within pumping chamber 18. As the volume within the pumping chamber decreases, the pressure within the pumping chamber increases to overcome the bias exerted by spring 64 against ball check 62 and a precise amount of metered fluid is pumped from pumping chamber 18 through out-flow conduit 14 and tubing 12 to the patient. The fluid pressure necessary to open ball check 62 is determined in large part by the spring constant of spring 64.

Figure 4:
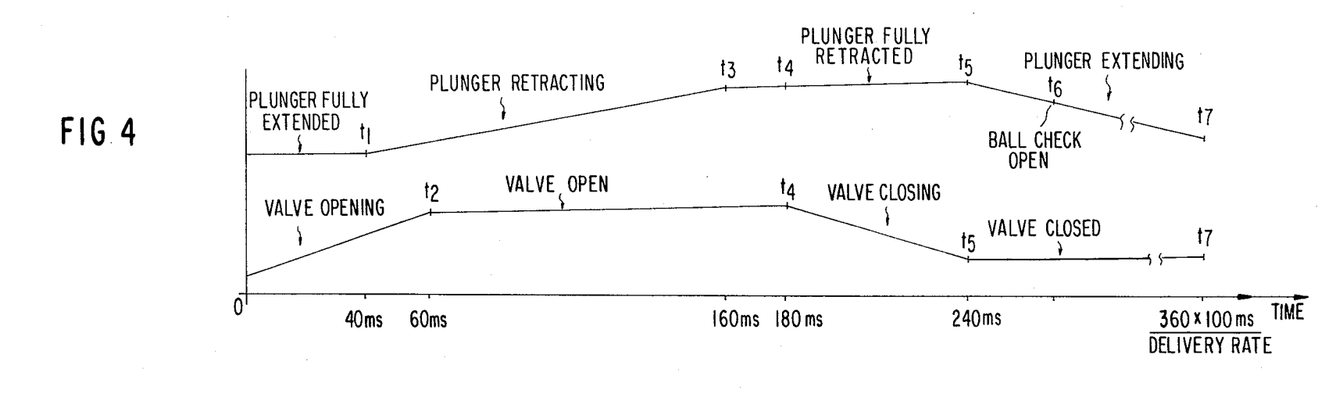
FIG. 4 is a graph representing the interrelated operating sequences of the valve stepping motor and the main stepping motor.

Turning to FIG. 4, the interrelationship between the reciprocal movements of valve actuator 32 and plunger 72 can be graphically seen. The pumping cycle is initiated at time $t_0$, with plunger 72 in a fully extended position, i.e., at the bottom of its stroke. Valve stepping motor 34 begins to step through a series of positions which serve to retract valve actuator 32 and open inlet port 22. The energization of main stepping motor 74 is programmed into motor controller 48 such that plunger 72 also begins retracting at time $t_1$ part-way through the valve actuator retraction sequence. At time $t_2$ shortly after time $t_1$, valve actuator 32 reaches a fully open or retracted position to enable the flow of fluid from fluid in-flow conduit 6 to pumping chamber 18 and valve stepping motor 34 is de-energized by a signal from motor controller 48. Meanwhile, main stepping motor 74 continues stepping through a series of positions to retract plunger 72. At time $t_3$ plunger 72 reaches the fully retracted position at the top of its stroke and main stepping motor 74 is de-energized by a second signal from motor controller 48. Valve actuator 32 remains fully retracted for an additional interval until time $t_4$. This additional interval allows the resilient diaphragm 20 to return to a relatively relaxed or undeformed state following the retraction of plunger 72. Hence, the difference between time $t_4$ and time $t_3$ should be greater than the relaxation time associated with the particular material used in fabricating resilient diaphragm 20.

At time $t_4$, valve stepping motor 34 is re-energized by a control signal from motor controller 48 and begins stepping through various incremental steps until time $t_5$ when valve actuator 32 reaches a fully extended position to seal off inlet port 22. Once the valve actuator is in its fully extended position, valve stepping motor 34 is again de-energized to await the beginning of the next pumping cycle. Simultaneous with the sealing of inlet port 22 at time $t_5$, main stepping motor 74 is re-energized and shifts through several incremental steps, driving plunger 72 in a downward direction to provide the pressure necessary for overcoming the bias on ball check 62. At time $t_6$, the ball check unseats to open outlet port 58. Fluid is subsequently discharged from pumping chamber 18 through the outlet port until time $t_7$, when plunger 72 reaches its fully extended position at the bottom of the plunger stroke to complete the pumping cycle. The period of time from $t_0$ to $t_6$ is characterized as the pumping cycle refill phase, i.e., that portion of the pumping cycle dedicated to refilling pumping chamber 18 with fluid in preparation for delivery of the fluid to the patient, while the period of time between $t_6$ and $t_7$ is characterized as the pumping cycle delivery phase. The pumping cycle refill phase in turn includes the interval from time $t_5$ to time $t_6$ given over to pressurizing pumping chamber 18, which interval is designated the pumping cycle pressurizing phase.

Unless otherwise corrected, the interruption of fluid flow which occurs during the refill phase of the pumping cycle can lead to the formation of fluid pulses in the outflow conduit 14 of fluid metering device 2 and tubing 12. Such pulses are undesirable, particularly where the fluid involved is a rapidly metabolized drug capable of producing near instantaneous physiological reaction in the patient. Pulsatile fluid delivery can be significantly attenuated, however, and an essentially continuous flow of fluid between metering device 2 and the patient can be established, by making the time required for completing the refill phase as short as possible relative to the time required to carry out the fluid delivery phase. There is little room for compression of the refill phase itself because the time from $t_0$ to $t_5$ used for actually refilling pumping chamber 18 with fluid is substantially fixed by the geometry of the pumping chamber. Only the pressurizing portion of the refill phase can be reduced, through the expedient of driving main stepping motor 74 at an increased speed between time $t_5$ and $t_6$. The greater advantage of the present control procedure lies in adjusting the operation of the main stepping motor during the delivery phase in order to stretch out the downward stroke of plunger 72 as long as possible, subject to the constraint imposed by the necessity to pump enough fluid within a specific interval to meet the desired fluid delivery rate. This stretching out of the plunger downstroke may be accomplished, for example, by setting $t_7$ equal to some constant divided by the desired fluid delivery rate. That is:

$$t_7 = k/RATE,$$

where k is a constant chosen on the basis of the pumping chamber geometry and RATE is a value representing the desired rate of fluid delivery. In this manner, the pulsatile effects of the discontinuity in fluid delivery associated with the refill phase are minimized over the entire pumping cycle.

Figure 5:
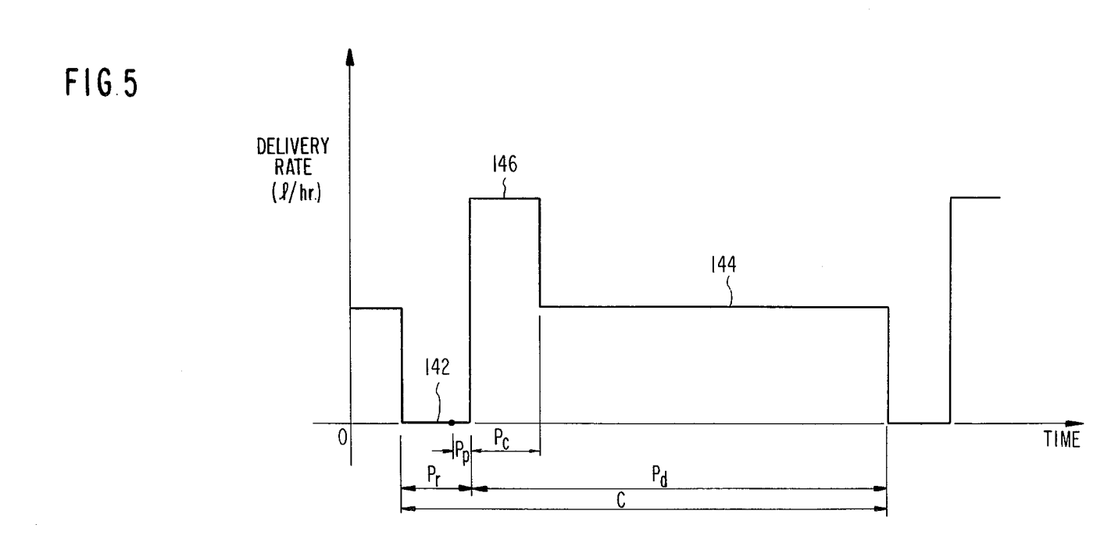
FIG. 5 is a graph illustrating the changes in fluid delivery rate which occur over a single pumping cycle when the control procedure of the present invention is implemented in the fluid delivery system of FIGS. 1, 2 and 3.

FIG. 5 graphically illustrates the rate of fluid delivery from fluid metering device 2 as a function of time. Throughout most of the refill phase $P_r$ of each pumping cycle C, valve actuator 32 is in an open position and fluid passes through inlet port 22 into pumping chamber 18. Plunger 72 is either retracting or completely retracted and ball check 62 is closed to prevent any fluid from leaving pumping chamber 18. Moreover, the passage of fluid from pumping chamber 18 continues to be blocked for a short interval near the end of the refill phase $P_r$, as plunger 72 begins its downstroke and the pressure in pumping chamber 18 builds to a value sufficient to open ball check 62. This latter interval is the pressurizing phase $P_p$. Of course, the delivery rate during the entire refill phase $P_r$, including the pressurizing phase $P_p$, is zero as indicated at 142 in FIG. 5. During the remainder or delivery phase $P_d$ of the pumping cycle, plunger 72 is reciprocating toward a fully extended position to depress resilient diaphragm 20 and pump fluid from pumping chamber 18 past the now-open ball check 62. According to the teachings of the present invention, main stepping motor 74 is controlled such that plunger 72 moves through the downstroke at a constant velocity for most of the delivery phase $P_d$. Hence, as indicated at 144 in FIG. 5, the fluid delivery rate during delivery phase $P_d$ is largely constant. In order to compensate for the fact that no fluid is delivered from pumping chamber 18 during the refill phase $P_r$, however, it is necessary for a short period after the initiation of the delivery phase $P_d$ to provide an increased fluid delivery rate, designated 146 in FIG. 5. This momentarily high delivery rate 146 occurs during a catch-up phase $P_c$ immediately following the onset of the delivery phase $P_d$, and it can be seen upon reflection that the net effect of high delivery rate 146 is to keep the average delivery rate for the entire pumping cycle as close as possible to the time-linear or constant delivery rate 144. The implementation of a catch-up phase $P_c$, then, further contributes to the desired goal of providing an essentially continuous or time-linear flow of fluid between fluid metering device 2 and the patient.

Figure 6:
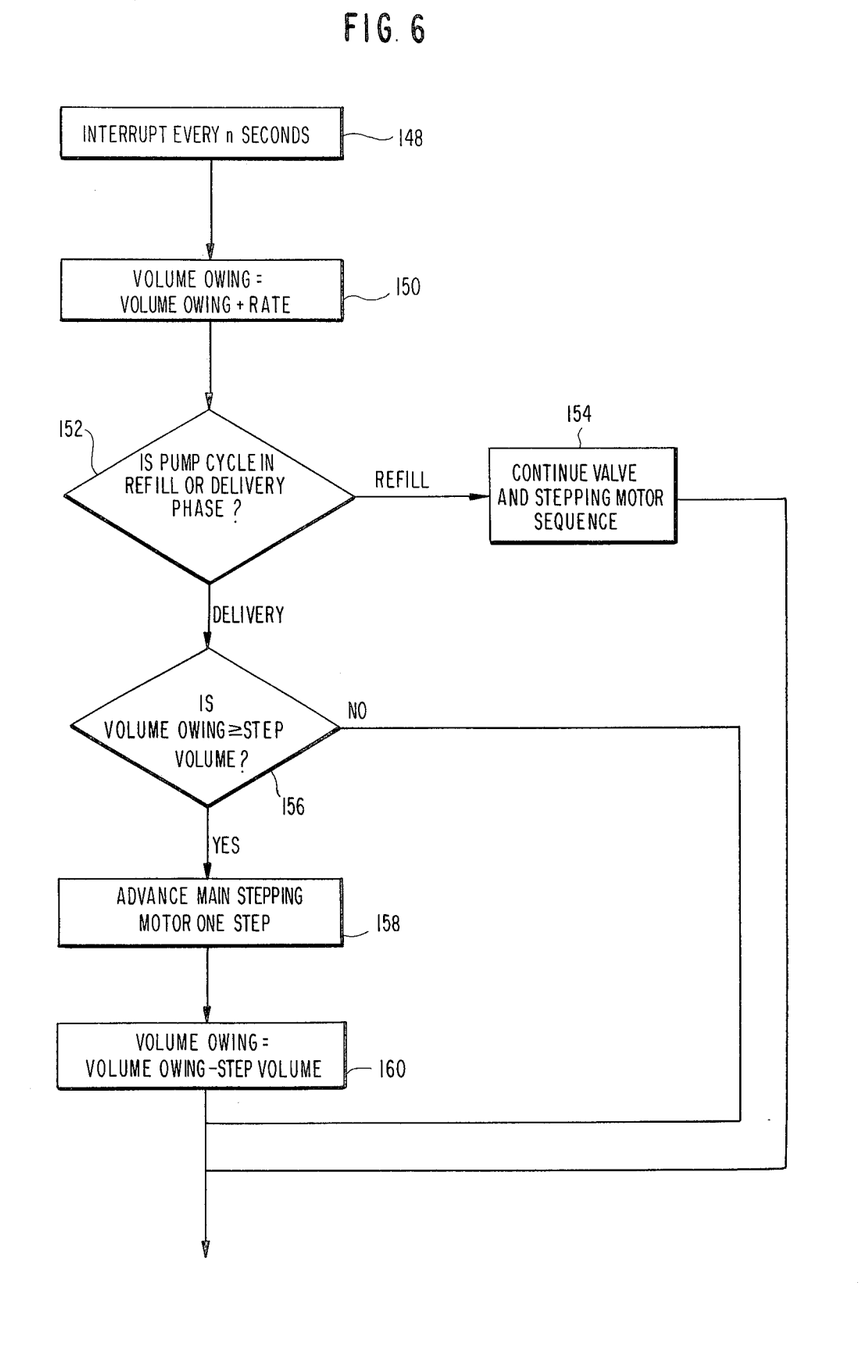
FIG. 6 is a flow-chart illustrating one method for achieving the fluid delivery rates graphically depicted in FIG. 5.

One method for achieving the appropriate high delivery rate during the catch-up phase of the pumping cycle is outlined in flow chart form in FIG. 6. The FIG. 6 method is basically an accounting procedure, whereby a running tally is kept of the amount of fluid which should be delivered from pumping chamber 18 in order to maintain an essentially time-linear average delivery rate throughout the pumping cycle. The running tally is used at the end of the refill phase to drive the main stepping motor 74 at an increased speed until the actual deficit in fluid delivery caused by the refill phase is overcome. At this point, the main stepping motor is driven at a normal speed to provide the essentially constant fluid delivery rate indicated at 144 in FIG. 5.

A VOLUME OWING register in microprocessor 92 is first designated to accumulate rate-representative signals RATE at predetermined intervals in the pumping cycle. In the preferred embodiment of the present invention, the RATE signal is directly proportional to the desired fluid delivery rate. As indicated at program block 148 of FIG. 6, the control sequence implemented in motor controller 48 is interrupted every n seconds, where n is a fractional value representing a time interval much smaller than the length of the refill phase. At each such interruption, the RATE signal is added to the VOLUME OWING register, indicated at program block 150 of FIG. 6, and a determination is subsequently made as to whether the pumping cycle is in the refill phase or the delivery phase. This determination, which is indicated at program block 152, can be based on the sensed incremental step position of main stepping motor 74. That is, if main stepping motor 74 is at an incremental step position other than those incremental step positions associated with the delivery phase $P_d$ of pumping cycle C, the pumping cycle is in a refill phase.

During the refill phase of the pumping cycle, the determination at program block 152 results in continued shifting of valve stepping motor 34 through its incremental steps, indicated at program block 154. The motor control process of FIG. 6 then returns to the process starting point at program block 148 to await the next control sequence interruption. In this manner, the RATE signal is added to the VOLUME OWING register every n seconds and the amount in the VOLUME OWING register progressively increases or accumulates throughout the refill phase. When, however, it is determined at program block 152 that the refill phase has ended and the fluid delivery phase has begun, a comparison, indicated at program block 156, is made between the accumulated amount in the VOLUME OWING register and a predetermined value STEP VOLUME. STEP VOLUME represents the average volume of fluid discharged from pumping chamber 18 for each incremental step taken by main stepping motor 74 during the delivery phase of the pumping cycle. If the amount in the VOLUME OWING register is greater than or equal to the value of STEP VOLUME, main stepping motor 74 is advanced one step, indicated at program block 158, and the amount in the VOLUME OWING register is decreased by the value of STEP VOLUME, as indicated at program block 160. The comparison at program block 156 is now repeated at n second intervals, advancing main stepping motor 74 through a series of incremental steps also at n second intervals to discharge fluid from pumping chamber 18 at the high delivery rate 146 illustrated in FIG. 5. This high delivery rate continues until the total volume of fluid so discharged compensates for the interruption in fluid flow which occurs during the refill phase, i.e., until the amount in the VOLUME OWING register is depleted to a value less than the value STEP VOLUME representing the volume of fluid discharged from pumping chamber 18 by a single main stepping motor step. At this point, the main stepping motor operation of program block 158 is bypassed and the amount in the VOLUME OWING register begins to accumulate until it exceeds the value of STEP VOLUME and the motor is once again advanced through an incremental step at program block 158. The latter situation, wherein the volume of fluid discharged from pumping chamber 18 keeps pace with the amount accumulating in the VOLUME OWING register, occurs during that portion of the delivery phase characterized by the essentially constant fluid delivery rate 144 of FIG. 5.

Figure 7:
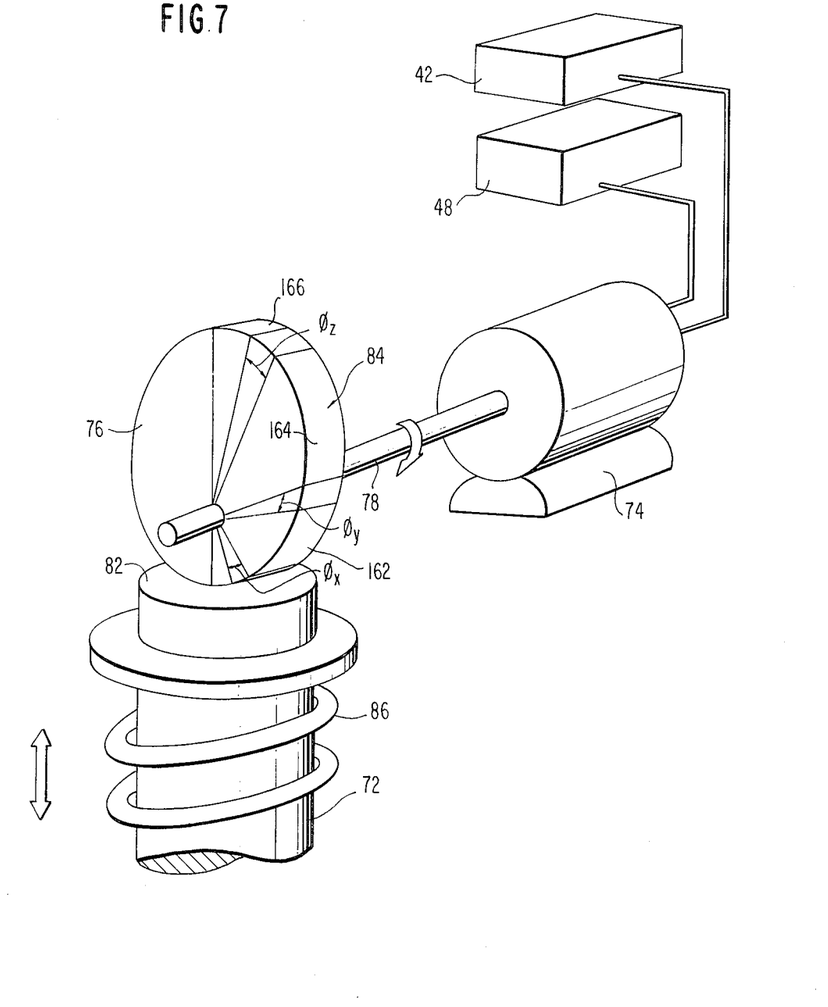
FIG. 7 provides a perspective view of the mechanical interface between the cam connected to the main stepping motor and the plunger which reciprocates to furnish a rectilinear pumping force in response to the rotation of the cam.

An additional factor involved in maintaining a time-linear average delivery rate arises from the mechanical interrelationship between cam 76 and plunger 72. FIG. 7 provides a close up illustration of cam 76 including camming surface 84 and shaft 78 connecting cam 76 to main stepping motor 74. Main stepping motor 74 rotates through a series of steps in response to control signals received from motor controller 48. Each of the steps is angularly displaced from the succeeding step by an equal amount. Hence, as main stepping motor 74 moves from step to step, shaft 78 and cam 76 also undergo a series of equal angular displacements. In the preferred embodiment of the present invention, main stepping motor 74 has twenty-four steps per half-revolution, the twenty-four steps serving to drive plunger 72 from the fully retracted position through the downstroke to the fully extended position. The motor is next reversed and driven through the same twenty-four steps in reverse order to guide plunger 72 from the fully extended position through the upstroke back to the fully retracted position. For the sake of simplicity, only representative angular displacements $\phi_x$, $\phi_y$ and $\phi_z$ are shown in FIG. 7. As previously indicated, all of these angular displacements are equal. However, due to the interrelationship between the shaft 78, camming surface 84 and plunger 72, equal angular displacements of cam 76 do not produce equal rectilinear movements of the plunger. Those angular displacements $\phi_x$ which occur during the first few motor steps, when the lower portion 162 of camming surface 84 is in contact with plunger 72, produce less rectilinear movement of the plunger than do those angular displacements $\phi_y$ which occur during intermediate motor steps when the middle portion 164 of camming surface 84 is in contact with the plunger. The motor steps which produce angular displacements $\phi_z$ near the mid-point of each motor revolution, when the upper portion 166 of camming surface 84 is in contact with plunger 72 at the end of the plunger downstroke, likewise result in relatively less rectilinear movement of the plunger per motor step.

Figure 8:
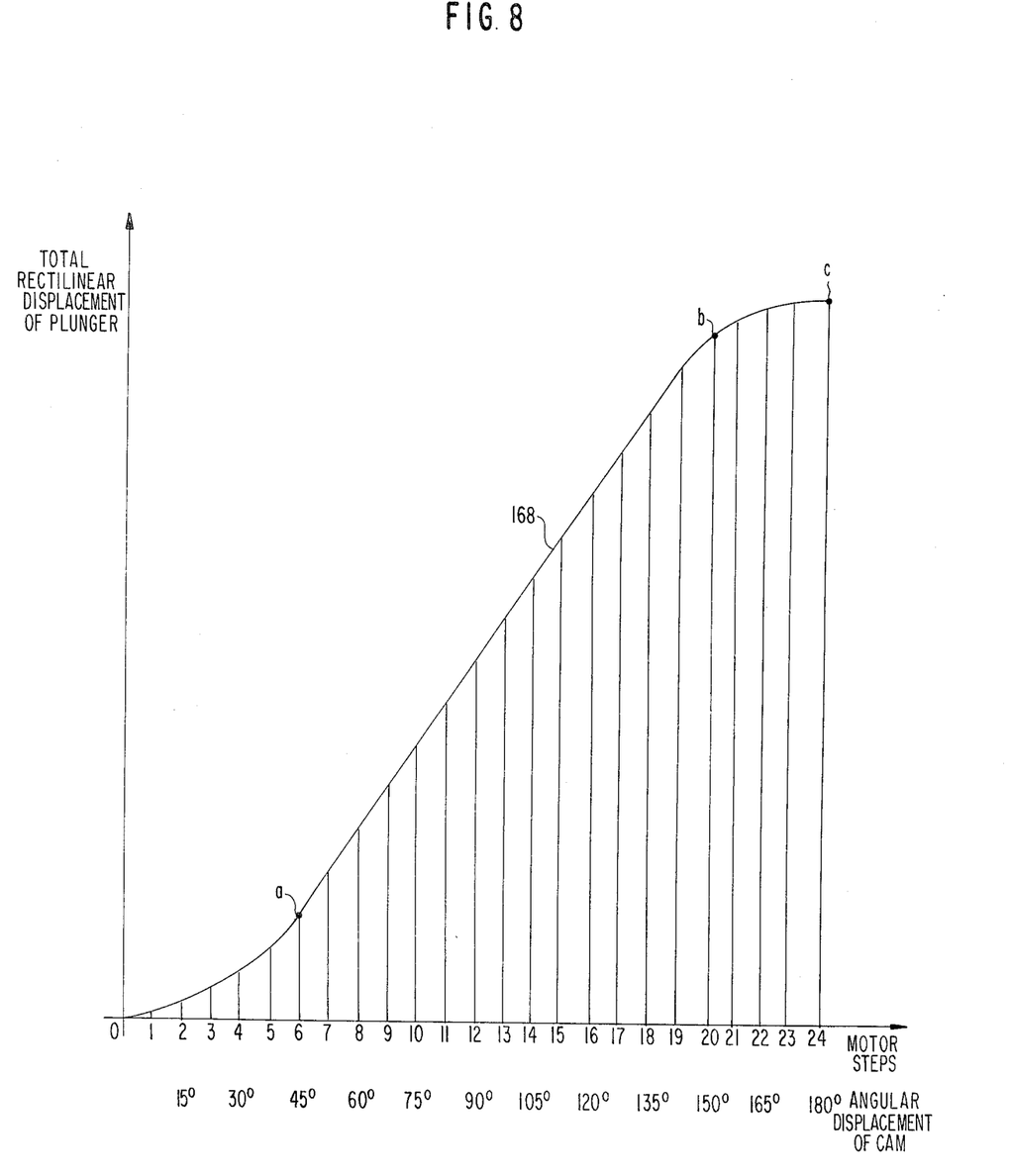
FIG. 8 is a graphic illustration of the camming curve associated with the cam of FIG. 7.

The camming curve 168 of FIG. 8 graphically illustrates the relationship between motor steps and rectilinear plunger displacement during the plunger downstroke. In the preferred embodiment of the present invention, main stepping motor 74 has twenty-four steps per half-revolution. There are three distinctly different camming phases evident from the camming curve 168. The first phase occurs at the outset of each pumping cycle, as main stepping motor 74 rotates through its initial steps to point a. It will be recalled that the rectilinear displacement of plunger 72 during this first phase is minimal. The second camming phase, between points a and b, is characterized by the rotation of main stepping motor 74 through its intermediate motor steps and the movement of plunger 72 on the downstroke is approximately linear, i.e., plunger 72 is displaced by an equal amount for each angular displacement of cam 74. From point b until point c marking the fully extended plunger position at the twenty-fourth motor step, the rectilinear displacement of plunger 72 per step is again non-linear, progressively decreasing until the fully extended plunger position is reached.

During the second camming phase, where the rectilinear displacement of plunger 72 proceeds in approximately equal increments for each motor step, the volume of fluid expelled from pumping chamber 18 at each motor step is also approximately equal. On the other hand, the volume of fluid expelled from the pumping chamber per motor step during the first and third camming stages varies substantially between motor steps. It is therefore evident that the stepping speed of main stepping motor 74 must be varied from camming phase to camming phase if the volume expelled from pumping chamber 18 per unit of time is to remain constant throughout the pumping cycle. This is accomplished in the preferred embodiment of the present invention by programming motor controller 48 to increase the speed at which main stepping motor 74 is driven through its incremental steps in the forward direction during the first and third camming phases. Where main stepping motor 74 is characterized by twenty-four steps per half-revolution, the first camming phase occurs over approximately the first six motor steps, while the last four motor steps constitute the third camming phase. Motor controller 48 is accordingly designed to drive main stepping motor 74 at increased speeds whenever the main stepping motor is at steps one through six or twenty through twenty-four of the forward direction. It should also be noted with regard to the fluid metering device of FIG. 2 that the first six steps of main stepping motor 74 coincide with the pressurizing phase $P_p$ of the pumping cycle C illustrated in FIG. 5. Consequently, driving the main stepping motor at higher speeds during motor steps one through six to compensate for the effects of the first camming phase simultaneously shortens the refill phase $P_r$ of the pumping cycle in the manner previously contemplated. Upon leaving the high speed control sequence mode associated with the first camming phase, then, the motor controller 48 will move directly into the high speed control sequence mode associated with the pumping cycle catch-up phase $P_c$ of FIG. 5 before reaching the reduced speed control sequence mode normally associated with the second camming phase of FIG. 8.

The entire stepping motor control procedure of the present invention may be carried out via either dedicated hardware or programmable hardware using appropriate software routines. One such software routine for accomplishing the stepping motor control procedure discussed in connection with FIGS. 3–8 is outlined as follows:

```
00060 00717         **************************************************************
00070 00718         *       MODULE MECH          16H10 JUNE 19, 1981    ED SOLOMON    *
00080 00719         *                                                                 *
00090 00720         *       SUBROUTINES:         VOLOWC  - VOLUME OWING CALCULATE     *
00100 00721         *                            PMPHOM  - PUMP HOME                  *
00110 00722         *                            PMPRUN  - PUMP RUN                   *
00120 00723         *                            PFLGCV  - PLUNGER FLAG COVERED       *
00130 00724         *                            VFLGOP  - VALVE FLAG OPEN            *
00140 00725         *                            VCLOSD  - VALVE CLOSED               *
00150 00726         *                            VOPEN   - VALVE OPEN                 *
00160 00727         *                            PLUP    - PLUNGER UP                 *
00170 00728         *                            PLDN    - PLUNGER DOWN               *
00180 00729         *                            MTRSLP  - MOTOR SLIP                 *
00190 00730         *                            MPOWER  - MOTOR POWER                *
00200 00731         *                            BINSTP  - BINARY TO STEPPING MOTOR CODE *
00210 00732         **************************************************************

00230 00734         **************************************************************
00240 00735         *       PLUNGER UP   -> PLUNGER POSITION = 0                      *
00250 00736         *       PLUNGER DOWN -> PLUNGER POSITION = 24                     *
00260 00737         *       VALVE CLOSED -> VALVE POSITION = 0                        *
00270 00738         *       VALVE OPEN   -> VALVE POSITION = 12                       *
00280 00739         **************************************************************

00300 00741A 1300                          ORG     $1300
00320 00743        1300      A VOLOWC EQU  *
00330 00744                    * SUBROUTINE VOLOWC CALCULATES THE VOLUME OWING BY ADDING THE 3-DIGIT
00340 00745                    * RATE TO VOLOWE EVERY 5 MSEC FOR ADULT VERSION OR EVERY 50 MSEC FOR
00350 00746                    * PEDIATRIC VERSION, WHILE THE RUN FLAG IS SET.

00370 00748A 1300 0B 1F 29 132C   BRCLR   RUN$,RUN,RTRN14 IF RUN FLAG IS CLEAR, RETURN 00390 00750A 1303 0D 28 08 130E   BRCLR   PED$,PED,CON115 IF PEDIATRIC FLAG SET,
00400 00751A 1306 3A 36       A   DEC     DECTMR      DECREMENT DECIMAL TIMER
00410 00752A 1308 2A 22  132C     BPL     RTRN14      IF MINUS,
00420 00753A 130A A6 09       A   LDA     #9          SET DECIMAL TIMER TO 9
00430 00754A 130C B7 36       A   STA     DECTMR 00450 00756                    * ADD 3-DIGIT RATE TO VOLOWE (VOLUME OWING)
00460 00757A 130E AE 02    A CON115 LDX   #2
00470 00758A 1310 E6 3C    A NEXT01 LDA   RATE,X      LOAD A DIGIT OF RATE INTO A REGISTER
00480 00759A 1312 EB 38    A        ADD   VOLOWE+1,X  ADD CORRESPONDING DIGIT OF VOLOWE
00490 00760A 1314 A1 0A    A        CMP   #10         TEST FOR BCD OVERFLOW
00500 00761A 1316 25 04   131C      BLO   CON118      SKIP OVERFLOW CORRECTION IF LESS THAN 10
00510 00762A 1318 A0 0A    A        SUB   #10         CORRECT DIGIT
00520 00763A 131A 6C 37    A        INC   VOLOWE,X    CARRY BY INCREMENTING NEXT SIGNIFICANT DIGIT
00530 00764A 131C E7 3B    A CON118 STA   VOLOWE+1,X  STORE DIGIT BACK IN VOLOWE
00540 00765A 131E 5A       A        DECX              SELECT NEXT SIGNIFICANT DIGIT
00550 00766A 131F 2A EF  1310      BPL   NEXT01      RETURN TO ADD NEXT PAIR OF DIGITS IF NOT AT
00560 00767                    *                      MOST SIGNIFICANT DIGIT ALREADY 00580 00769                    * TEST FOR VOLOWE < 72000
00590 00770A 1321 B6 37    A        LDA   VOLOWE      COMPARE THOUSANDS DIGIT OF VOLOWE
00600 00771A 1323 A1 48    A        CMP   #72         WITH 72
00610 00772A 1325 25 05   132C     BLO   RTRN14       IF GREATER THAN OR EQUAL,
00620 00773A 1327 A6 19    A        LDA   #VLOWFL     SET FAILURE NUMBER
00630 00774A 1329 CD 1700  A        JSR   FAIL 00650 00776A 132C 81               RTRN14 RTS
00670 00778       132D     A PMPHOM EQU   *
00680 00779                    * SUBROUTINE PMPHOM HOMES THE PUMP MECHANISM. FIRST, THE VALVE IS HOMED
00690 00780                    * TO THE OPEN POSITION, THEN THE PLUNGER IS HOMED TO THE UP POSITION.
```

```
00710 00782A 132D 01 2E 0A 133A           BRCLR    VINC$,HOMFLG,VDEC IF VALVE INCREMENT FLAG IS SET,
00720 00783                              * INCREMENT VALVE UNTIL FLAG IS OPEN OR 64 STEPS HAVE BEEN TAKEN
00730 00784A 1330 09 28 13 1346           BRCLR    VFLAG$,VFLAG,CON121 IF VALVE FLAG IS COVERED
00740 00785A 1333 3C 33        A          INC      VALVE    INCREMENT VALVE
00750 00786A 1335 0D 33 02 133A           BRCLR    6,VALVE,VDEC IF BIT 6 OF VALVE IS SET (->VALVE=64)
00760 00787A 1338 38 2E        A          LSL      HOMFLG   DISABLE FURTHER VALVE INCREMENTING AND
00770 00788                              *                  ENABLE VALVE DECREMENTING 00790 00790A 133A 03 2E 13 1350  VDEC     BRCLR    VDEC$,HOMFLG,VHOME IF VALVE DECREMENT FLAG IS SET,
00800 00791                              * DECREMENT VALVE UNTIL FLAG IS OPEN OR 64 STEPS HAVE BEEN TAKEN
00810 00792A 133D 09 28 06 1346           BRCLR    VFLAG$,VFLAG,CON121 IF VALVE FLAG IS COVERED
00820 00793A 1340 3A 33        A          DEC      VALVE    DECREMENT VALVE
00830 00794A 1342 2A 0C        1350       BPL      VHOME    IF NEGATIVE,
00840 00795A 1344 20 21        1367       BRA      CON127   SET FAILURE NUMBER 00860 00797                              * WHEN VALVE FLAG IS FIRST UNCOVERED,
00870 00798A 1346 3F 2E        A CON121   CLR      HOMFLG   DISABLE VALVE INCREMENTING OR DECREMENTING
00880 00799A 1348 14 2E        A          BSET     VHOME$,HOMFLG ENABLE VALVE HOMING
00890 00800A 134A B6 33        A          LDA      VALVE
00900 00801A 134C A4 03        A          AND      #%00000011 CLEAR VALVE POSITION EXCEPT FOR 2 LSBITS
00910 00802A 134E B7 33        A          STA      VALVE    (MAINTAIN PHASING)

00930 00804A 1350 05 2E 19 136C  VHOME    BRCLR    VHOME$,HOMFLG,PINC IF VALVE HOME FLAG SET,
00940 00805                              * INCREMENT VALVE UNTIL VALVE FLAG IS COVERED OR 28-31 STEPS HAVE BEEN
00950 00806                              * TAKEN 00970 00808                              * TEST IF VALVE = 4N + 1 (N = INTEGER)
00980 00809A 1353 01 33 0C 1362           BRCLR    0,VALVE,CON124 IF BIT 0 OF VALVE IS SET,
00990 00810A 1356 02 33 09 1362           BRSET    1,VALVE,CON124 IF BIT 1 OF VALVE IS CLEAR, 01010 00812A 1359 09 28 06 1362           BRCLR    VFLAG$,VFLAG,CON124 IF VALVE FLAG COVERED,
01020 00813A 135C A6 0B        A          LDA      #11
01030 00814A 135E B7 33        A          STA      VALVE    SET VALVE POSITION TO 11 (SET TO 12 AT CON124
01040 00815                              *                   AHEAD)
01050 00816A 1360 38 2E        A          LSL      HOMFLG   DISABLE FURTHER VALVE OPENING AND
01060 00817                              *                   ENABLE PLUNGER INCREMENTING
01070 00818A 1362 3C 33        A CON124   INC      VALVE    INCREMENT VALVE 01090 00820A 1364 0B 33 05 136C           BRCLR    5,VALVE,PINC IF BIT 5 OF VALVE IS SET (->VALVE=32)
01100 00821A 1367 A6 20        A CON127   LDA      #VHOMFL  SET FAIL NUMBER
01110 00822A 1369 CD 170D      A          JSR      FAIL 01130 00824A 136C 07 2E 18 1387  PINC     BRCLR    PINC$,HOMFLG,PHOME IF PLUNGER INCREMENT FLAG SET,
01140 00825                              * INCREMENT PLUNGER UNTIL FLAG COVERED OR 64 STEPS HAVE BEEN TAKEN
01150 00826A 136F 06 28 0B 137D           BRSET    PFLAG$,PFLAG,CON133 IF PLUNGER FLAG IS COVERED
01160 00827A 1372 3C 30        A          INC      PLUNGR   INCREMENT PLUNGER 01180 00829A 1374 0D 30 10 1387           BRCLR    6,PLUNGR,PHOME IF BIT 6 OF PLUNGER IS SET (->PLUNGER=64)
01190 00830A 1377 A6 21        A CON130   LDA      #PHOMFL  SET THE FAILURE NUMBER
01200 00831A 1379 CD 170D      A          JSR      FAIL
01210 00832A 137C 81                      RTS 01230 00834A 137D 38 2E        A CON133   LSL      HOMFLG   DISABLE PLUNGER INCREMENTING AND
01240 00835                              *                   ENABLE PLUNGER HOMING
01250 00836A 137F B6 30        A          LDA      PLUNGR
01260 00837A 1381 A4 03        A          AND      #%00000011 CLEAR PLUNGER POSITION EXCEPT FOR 2 LSBITS
01270 00838                              *                   (MAINTAIN PHASING)
01280 00839A 1383 AB 30        A          ADD      #48      ADD 48 TO PLUNGER POSITION
01290 00840A 1385 B7 30        A          STA      PLUNGR 01310 00842A 1387 09 2E 14 139E  PHOME    BRCLR    PHOME$,HOMFLG,RTRN21 IF PLUNGER HOMING FLAG SET,
01320 00843                              * DECREMENT PLUNGER UNTIL PLUNGER FLAG OPEN OR 48 STEPS HAVE BEEN TAKEN 01340 00845                              * TEST IF PLUNGER = 4N + 3 (N = INTEGER)
01350 00846A 138A 01 30 0D 139A           BRCLR    0,PLUNGR,CON136 IF BIT 0 OF PLUNGER IS SET,
01360 00847A 138D 03 30 0A 139A           BRCLR    1,PLUNGR,CON136 IF BIT 1 OF PLUNGER IS SET, 01380 00849A 1390 06 28 07 139A           BRSET    PFLAG$,PFLAG,CON136 IF PLUNGER FLAG OPEN
01390 00850A 1393 3F 30        A          CLR      PLUNGR   SET PLUNGER POSITION TO 0
01400 00851A 1395 3F 2E        A          CLR      HOMFLG   DISABLE HOMING
01410 00852A 1397 18 2D        A          BSET     VLVCL$,CYCFLG ENABLE VALVE CLOSING
01420 00853A 1399 81                      RTS
01430 00854A 139A 3A 30        A CON136   DEC      PLUNGR   DECREMENT PLUNGER
01440 00855A 139C 27 D9        1377       BEQ      CON130   IF NON-ZERO,
01450 00856A 139E 81                RTRN21 RTS              RETURN
01470 00858                139F  A PMPRUN EQU      *
01480 00859                              * SUBROUTINE PMPRUN CONTROLS THE STEPPING SEQUENCE FOR THE VALVE AND
01490 00860                              * PLUNGER MOTORS 01510 00862                              * TEST FOR MACHINE IN DELIVERY MODE
01520 00863A 139F 0D 2D 2E 13D0           BRCLR    DELIV$,CYCFLG,PRSRZ
```

```
01540 00865                             * TEST FOR VOLOWE GREATER THAN OR EQUAL TO 5000
01550 00866                             * IF TRUE, SUBTRACT 4500 AND TAKE A MOTOR STEP
01560 00867                             * IF FALSE, SKIP MOTOR STEP
01570 00868A 13A2 AE 37      A              LDX    @VOLOWE
01580 00869A 13A4 F6                        LDA    ,X          LOAD THOUSANDS NUMBER OF VOLOWE INTO A REGISTER
01590 00870A 13A5 A0 05      A              SUB    @5          SUBTRACT 5 (THOUSAND)
01600 00871A 13A7 2B 27     13D0             BMI    PRSRZ
01610 00872A 13A9 F7                        STA    ,X          RETURN THOUSANDS NUMBER BACK TO VOLOWE
01620 00873A 13AA E6 01      A              LDA    1,X         LOAD HUNDREDS DIGIT INTO A REGISTER
01630 00874A 13AC AB 05      A              ADD    @5          ADD 5 (HUNDRED)
01640 00875A 13AE A1 0A      A              CMP    @10         TEST FOR BCD OVERFLOW
01650 00876A 13B0 25 03     13B5             BLO    CON139      SKIP OVERFLOW CORRECTION IF LESS THAN 10
01660 00877A 13B2 A0 0A      A              SUB    @10         SUBTRACT 10 (HUNDRED)
01670 00878A 13B4 7C                        INC    ,X          CARRY BY INCREMENTING THOUSANDS
01680 00879A 13B5 E7 01      A CON139 STA   1,X          RETURN HUNDREDS DIGIT BACK TO VOLOWE 01700 00881                             * ROUTINE FOR FLUID DELIVERY 01720 00883                             * TEST FOR PLUNGER FLAG COVERED AT POSITION 13
01730 00884A 13B7 B6 30      A              LDA    PLUNGR      COMPARE PLUNGER POSITION
01740 00885A 13B9 A1 0D      A              CMP    @13         WITH 13
01750 00886A 13BB 26 03     13C0             BNE    CON142      IF EQUAL,
01760 00887A 13BD CD 1469    A              JSR    FFLGCV      TEST FOR PLUNGER FLAG COVERED 01780 00889A 13C0 3C 30      A CON142 INC   PLUNGR      ADVANCE PLUNGER 1 STEP
01790 00890A 13C2 B6 30      A              LDA    PLUNGR      COMPARE PLUNGER POSITION
01800 00891A 13C4 A1 15      A              CMP    @21         WITH 21
01810 00892A 13C6 26 08     13D0             BNE    PRSRZ       IF EQUAL,
01820 00893A 13C8 1D 2D      A              BCLR   DELIV$,CYCFLG DISABLE FURTHER DELIVERY
01830 00894A 13CA 10 2D      A              BSET   FIN$,CYCFLG ENABLE FINISH DELIVERY ROUTINE
01840 00895A 13CC 3A 30      A              DEC    PLUNGR      SET PLUNGER POSITION TO 20

01860 00897A 13CE 16 57      A              BSET   PMSR$,PMSR SET PRESSURE MEASURE FLAG 01880 00899A 13D0 0B 2D 18 13EB PRSRZ BRCLR PRSRZ$,CYCFLG,VLVCL
01890 00900                             * ROUTINE FOR PRESSURIZING CASSETTE 01910 00902                             * TEST FOR VALVE CLOSED WHEN PLUNGER AT POSITION 2
01920 00903A 13D3 B6 30      A              LDA    PLUNGR      COMPARE PLUNGER POSITION
01930 00904A 13D5 A1 02      A              CMP    @2          WITH 2
01940 00905A 13D7 26 06     13DF             BNE    CON145      IF EQUAL,
01950 00906A 13D9 CD 147B    A              JSR    VCLOSD      TEST FOR VALVE CLOSED
01960 00907A 13DC 0B 2D 0C 13EB            BRCLR  PRSRZ$,CYCFLG,VLVCL IF PRESSURIZE FLAG IS CLEAR (CAN BE
01970 00908                             *                                 CLEARED BY SUBROUTINE VCLOSD) BRANCH TO
01980 00909                             *                                 VLVCL 02000 00911A 13DF 3C 30      A CON145 INC   PLUNGR      ADVANCE PLUNGER 1 STEP
02010 00912A 13E1 B6 30      A              LDA    PLUNGR      COMPARE PLUNGER POSITION
02020 00913A 13E3 A1 05      A              CMP    @5          WITH 5
02030 00914A 13E5 26 04     13EB             BNE    VLVCL       IF EQUAL,
02040 00915A 13E7 1B 2D      A              BCLR   PRSRZ$,CYCFLG DISABLE FURTHER PRESSURIZATION
02050 00916A 13E9 1C 2D      A              BSET   DELIV$,CYCFLG ENABLE DELIVERY 02070 00918A 13EB 09 2D 11 13FF VLVCL BRCLR VLVCL$,CYCFLG,RLX
02080 00919                             * ROUTINE FOR CLOSING VALVE 02100 00921                             * TEST FOR VALVE FLAG OPEN AT POSITION 4
02110 00922A 13EE B6 33      A              LDA    VALVE       COMPARE VALVE POSITION
02120 00923A 13F0 A1 04      A              CMP    @4          WITH 4
02130 00924A 13F2 26 03     13F7             BNE    CON148      IF EQUAL,
02140 00925A 13F4 CD 1472    A              JSR    VFLGOP      TEST FOR VALVE FLAG OPEN 02160 00927A 13F7 3A 33      A CON148 DEC   VALVE       CLOSE VALVE 1 STEP
02170 00928A 13F9 26 04     13FF             BNE    RLX         TEST IF VALVE IS AT POSITION 0 - CLOSED
02180 00929A 13FB 19 2D      A              BCLR   VLVCL$,CYCFLG DISABLE FURTHER VALVE CLOSING
02190 00930A 13FD 1A 2D      A              BSET   PRSRZ$,CYCFLG ENABLE CASSETTE PRESSURIZATION 02210 00932A 13FF 07 2D 19 141B RLX   BRCLR RLX$,CYCFLG,RTRCT
02220 00933                             * ROUTINE TO WAIT FOR RUBBER DIAPHRAGM TO RELAX 02240 00935                             * TEST FOR PLUNGER UP WHEN RUBBER RELAXATION TIMER AT 2
02250 00936A 1402 B6 2F      A              LDA    RLXTMR      COMPARE RELAXATION TIMER
02260 00937A 1404 A1 02      A              CMP    @2          WITH 2
02270 00938A 1406 26 06     140E             BNE    CON151      IF EQUAL,
02280 00939A 1408 CD 14AD    A              JSR    PLUP        TEST FOR PLUNGER UP
02290 00940A 140B 07 2D 0D 141B           BRCLR  RLX$,CYCFLG,RTRCT IF RELAXATION FLAG IS CLEAR (CAN BE
02300 00941                             *                                 CLEARED BY SUBROUTINE PLUP) BRANCH TO
02310 00942                             *                                 RTRCT
```

```
02330 00944A 140E 3C 2F       A CON151 INC    RLXTMR    INCREMENT RUBBER RELAXATION TIMER
02340 00945A 1410 05 2F 08 141B       BRCLR  2,RLXTMR,RTRCT IF BIT 2 OF RELAXATION TIMER IS SET (->-4)
02350 00946A 1413 3F 2F       A       CLR    RLXTMR    CLEAR RUBBER RELAXATION TIMER
02360 00947A 1415 17 2D       A       BCLR   RLX$,CYCFLG DISABLE RUBBER RELAXATION WAIT ROUTINE
02370 00948A 1417 18 2D       A       BSET   VLVCL$,CYCFLG ENABLE VALVE CLOSING 02390 00950A 1419 18 57       A       BSET   PREF$,PREF SET PRESSURE REFERENCE FLAG 02410 00952A 141B 05 2D 13 1431 RTRCT BRCLR  RTRCT$,CYCFLG,VLVOP
02420 00953                          * ROUTINE TO RETRACT PLUNGER 02440 00955                          * ROUTINE TO TEST FOR PLUNGER COVERED AT POSITION 13
02450 00956A 141E B6 30       A       LDA    PLUNGR    COMPARE PLUNGER POSITION
02460 00957A 1420 A1 0D       A       CMP    #13       WITH 13
02470 00958A 1422 26 05       1429    BNE    CON154    IF EQUAL,
02480 00959A 1424 CD 1469     A       JSR    PFLGCV    TEST FOR PLUNGER FLAG COVERED 02500 00961A 1427 12 57       A       BSET   CYCMP$,CYCMP SET CYCLE COMPLETE FLAG 02520 00963A 1429 3A 30       A CON154 DEC   PLUNGR    RETRACT PLUNGER 1 STEP
02530 00964A 142B 26 04       1431    BNE    VLVOP     TEST IF PLUNGER IS AT POSITION 0
02540 00965A 142D 15 2D       A       BCLR   RTRCT$,CYCFLG DISABLE PLUNGER RETRACTION
02550 00966A 142F 16 2D       A       BSET   RLX$,CYCFLG ENABLE RUBBER RELAXATION WAIT ROUTINE 02570 00968A 1431 03 2D 25 1459 VLVOP BRCLR  VLVOP$,CYCFLG,FIN
02580 00969                          * ROUTINE TO OPEN VALVE 02600 00971                          * TEST FOR VALVE FLAG OPEN AT POSITION 9
02610 00972A 1434 B6 33       A       LDA    VALVE     COMPARE VALVE POSITION
02620 00973A 1436 A1 09       A       CMP    #9        WITH 9
02630 00974A 1438 26 03       143D    BNE    CON157    IF EQUAL,
02640 00975A 143A CD 1472     A       JSR    VFLGOP    TEST FOR VALVE FLAG OPEN 02660 00977                          * TEST FOR PLUNGER DOWN WHEN VALVE AT POSITION 2
02670 00978A 143D B6 33       A CON157 LDA   VALVE     COMPARE VALVE POSITION
02680 00979A 143F A1 02       A       CMP    #2        WITH 2
02690 00980A 1441 26 06       1449    BNE    CON160    IF EQUAL,
02700 00981A 1443 CD 14C6     A       JSR    PLDN      TEST FOR PLUNGER DOWN
02710 00982A 1446 03 2D 10 1459       BRCLR  VLVOP$,CYCFLG,FIN IF VALVE OPENING FLAG IS CLEAR (CAN BE
02720 00983                          *                CLEARED BY SUBROUTINE PLDN) BRANCH TO
02730 00984                          *                FIN 02750 00986A 1449 3C 33       A CON160 INC   VALVE     OPEN VALVE 1 STEP
02760 00987A 144B B6 33       A       LDA    VALVE     COMPARE VALVE POSITION
02770 00988A 144D A1 07       A       CMP    #7        WITH 7
02780 00989A 144F 26 02       1453    BNE    CON163    IF EQUAL,
02790 00990A 1451 14 2D       A       BSET   RTRCT$,CYCFLG ENABLE PLUNGER RETRACTION
02800 00991A 1453 A1 0C       A CON163 CMP   #12       COMPARE VALVE POSITION WITH 12
02810 00992A 1455 26 02       1459    BNE    FIN
02820 00993A 1457 13 2D       A       BCLR   VLVOP$,CYCFLG DISABLE FURTHER VALVE OPENING 02840 00995A 1459 01 2D 0C 1468 FIN   BRCLR  FIN$,CYCFLG,RTRN08
02850 00996                          * ROUTINE TO FINISH DELIVERY CYCLE
02860 00997A 145C 3C 30       A       INC    PLUNGR    ADVANCE PLUNGER 1 STEP
02870 00998A 145E B6 30       A       LDA    PLUNGR    COMPARE PLUNGER POSITION
02880 00999A 1460 A1 18       A       CMP    #24       WITH 24
02890 01000A 1462 26 04       1468    BNE    RTRN08    IF EQUAL,
02900 01001A 1464 11 2D       A       BCLR   FIN$,CYCFLG DISABLE FURTHER FINISH OF DELIVERY CYCLE
02910 01002A 1466 12 2D       A       BSET   VLVOP$,CYCFLG ENABLE VALVE OPENING
02920 01003A 1468 81                  RTRN08 RTS
02940 01005               1469      A PFLGCV EQU   *
02950 01006                          * SUBROUTINE PFLAGCV TESTS THAT THE PLUNGER FLAG IS COVERED
02960 01007A 1469 06 28 05 1471       BRSET  PFLAG$,PFLAG,RTRN16 IF PLUNGER FLAG OPEN,
02970 01008A 146C A6 17       A       LDA    #PLNGFL   SET THE FAILURE NUMBER
02980 01009A 146E CD 170D     A       JSR    FAIL
02990 01010A 1471 81                  RTRN16 RTS
03010 01012               1472      A VFLGOP EQU   *
03020 01013                          * SUBROUTINE VFLAGOP TESTS THAT THE VALVE FLAG IS OPEN
03030 01014A 1472 09 28 05 147A       BRCLR  VFLAG$,VFLAG,RTRN20 IF PLUNGER FLAG OPEN,
03040 01015A 1475 A6 16       A       LDA    #VALVFL   SET THE FAILURE NUMBER
03050 01016A 1477 CD 170D     A       JSR    FAIL
03060 01017A 147A 81                  RTRN20 RTS
03080 01019               147B      A VCLOSD EQU   *
03090 01020                          * SUBROUTINE VCLOSD CHECKS THAT THE VALVE IS CLOSED (VALVE FLAG COVERED).
03100 01021                          * IF THE VALVE IS NOT CLOSED THE ASSUMPTION IS THAT THE VALVE MOTOR HAS
03110 01022                          * SLIPPED A SECTOR (4 STEPS). THE SLIP FLAG IS SET, THE SLIP COUNTER IS
03120 01023                          * INCREMENTED, THE VALVE POSITION IS SET BACK TO 4 (ITS ASSUMED POSITION),
03130 01024                          * THE VALVE CLOSING ROUTINE IS RE-ENABLED AND THE CASSETTE PRESSURIZATION
03140 01025                          * SUSPENDED.
03150 01026                          * WHEN THIS ROUTINE IS CALLED A SECOND TIME, IF THE VALVE IS CLOSED
03160 01027                          * THE SLIP FLAG WILL BE CLEARED. IF THE VALVE IS STILL OPEN, A FAILURE
03170 01028                          * MESSAGE WILL RESULT.
```

```
03190 01030A 147B 08 28 08 1486          BRSET  VFLAG%,VFLAG,CON166 IF VALVE FLAG OPEN,
03200 01031A 147E 09 56 08 1489          BRCLR  SLIP$,SLIP,CON169 IF SLIP FLAG SET,
03210 01032A 1481 A6 16         A        LDA    #VALVFL
03220 01033A 1483 CD 170D       A        JSR    FAIL      SET FAILURE NUMBER
03230 01034A 1486 19 56         A CON166 BCLR   SLIP$,SLIP CLEAR THE SLIP FLAG
03240 01035A 1488 81                     RTS              RETURN 03260 01037                              * ROUTINE TO CATCH UP A SLIPPED VALVE MOTOR SECTOR
03270 01038A 1489 1B 2D         A CON169 BCLR   PRSRZ$,CYCFLG DISABLE FURTHER CASSETTE PRESSURIZATION
03280 01039A 148B 18 2D         A        BSET   VLVCL$,CYCFLG ENABLE VALVE CLOSING ROUTINE
03290 01040A 148D A6 04         A        LDA    #4
03300 01041A 148F B7 33         A        STA    VALVE     SET VALVE POSITION AT 4
03310 01042A 1491 AD 4C         14DF     BSR    MTRSLP    SET SLIP FLAG AND INCREMENT SLIP COUNTER
03320 01043A 1493 81                     RTS
03340 01045             1494    A VOPEN  EQU    *
03350 01046                              * SUBROUTINE VOPEN CHECKS THAT THE VALVE IS OPEN (VALVE FLAG COVERED).
03360 01047                              * IF THE VALVE IS NOT OPEN THE ASSUMPTION IS THAT THE VALVE MOTOR HAS
03370 01048                              * SLIPPED A SECTOR (4 STEPS). THE SLIP FLAG IS SET, THE SLIP COUNTER IS
03380 01049                              * INCREMENTED, THE VALVE POSITION IS SET BACK TO 8 (ITS ASSUMED POSITION),
03390 01050                              * THE VALVE OPENING ROUTINE IS RE-ENABLED AND THE PLUNGER RETRACTION
03400 01051                              * SUSPENDED.
03410 01052                              * WHEN THIS ROUTINE IS CALLED A SECOND TIME, IF THE VALVE IS OPEN
03420 01053                              * THE SLIP FLAG WILL BE CLEARED.  IF THE VALVE IS STILL NOT OPEN, A
03430 01054                              * FAILURE MESSAGE WILL RESULT.

03450 01056A 1494 08 28 08 149F          BRSET  VFLAG$,VFLAG,CON172 IF VALVE FLAG OPEN,
03460 01057A 1497 09 56 08 14A2          BRCLR  SLIP$,SLIP,CON175 IF SLIP FLAG SET,
03470 01058A 149A A6 16         A        LDA    #VALVFL
03480 01059A 149C CD 170D       A        JSR    FAIL      SET FAILURE NUMBER
03490 01060A 149F 19 56         A CON172 BCLR   SLIP$,SLIP CLEAR THE SLIP FLAG
03500 01061A 14A1 81                     RTS              RETURN 03520 01063                              * ROUTINE TO CATCH UP A SLIPPED VALVE MOTOR SECTOR
03530 01064A 14A2 15 2D         A CON175 BCLR   RTRCT$,CYCFLG DISABLE FURTHER PLUNGER RETRACTION
03540 01065A 14A4 12 2D         A        BSET   VLVOP$,CYCFLG ENABLE VALVE OPENING ROUTINE
03550 01066A 14A6 A6 08         A        LDA    #8
03560 01067A 14A8 B7 33         A        STA    VALVE     SET VALVE POSITION AT 8
03570 01068A 14AA AD 33         14DF     BSR    MTRSLP    SET SLIP FLAG AND INCREMENT SLIP COUNTER
03580 01069A 14AC 81                     RTS
03600 01071             14AD    A PLUP   EQU    *
03610 01072                              * SUBROUTINE PLUP CHECKS THAT THE PLUNGER IS UP (PLUNGER FLAG OPEN).
03620 01073                              * IF THE PLUNGER IS NOT UP THE ASSUMPTION IS THAT THE PLUNGER MOTOR HAS
03630 01074                              * SLIPPED A SECTOR (4 STEPS). THE SLIP FLAG IS SET, THE SLIP COUNTER IS
03640 01075                              * INCREMENTED, THE PLUNGER POSITION IS SET BACK TO 4 (ITS ASSUMED
03650 01076                              * POSITION, THE PLUNGER RETRACTION ROUTINE IS RE-ENABLED AND THE RUBBER
03660 01077                              * RELAXATION TIMING ROUTINE IS SUSPENDED.
03670 01078                              * WHEN THIS ROUTINE IS CALLED A SECOND TIME, IF THE PLUNGER IS UP
03680 01079                              * THE SLIP FLAG WILL BE CLEARED.  IF THE PLUNGER IS STILL NOT UP, A
03690 01080                              * FAILURE MESSAGE WILL RESULT.

03710 01082A 14AD 07 28 08 14B8          BRCLR  PFLAG$,PFLAG,CON178 IF PLUNGER FLAG CLOSED,
03720 01083A 14B0 09 56 08 14BB          BRCLR  SLIP$,SLIP,CON181 IF SLIP FLAG SET,
03730 01084A 14B3 A6 17         A        LDA    #PLNGFL
03740 01085A 14B5 CD 170D       A        JSR    FAIL      SET FAILURE NUMBER
03750 01086A 14B8 19 56         A CON178 BCLR   SLIP$,SLIP CLEAR THE SLIP FLAG
03760 01087A 14BA 81                     RTS              RETURN 03780 01089                              * ROUTINE TO CATCH UP A SLIPPED PLUNGER MOTOR SECTOR
03790 01090A 14BB 17 2D         A CON181 BCLR   RLX$,CYCFLG DISABLE FURTHER RELAXATION TIMING
03800 01091A 14BD 14 2D         A        BSET   RTRCT$,CYCFLG ENABLE PLUNGER RETRACTION ROUTINE
03810 01092A 14BF A6 04         A        LDA    #4
03820 01093A 14C1 B7 30         A        STA    PLUNGR    SET PLUNGER POSITION AT 4
03830 01094A 14C3 AD 1A         14DF     BSR    MTRSLP    SET SLIP FLAG AND INCREMENT SLIP COUNTER
03840 01095A 14C5 81                     RTS
03860 01097             14C6    A PLDN   EQU    *
03870 01098                              * SUBROUTINE PLDN CHECKS THAT THE PLUNGER IS DOWN (PLUNGER FLAG OPEN).
03880 01099                              * IF THE PLUNGER IS NOT DOWN THE ASSUMPTION IS THAT THE PLUNGER MOTOR HAS
03890 01100                              * SLIPPED A SECTOR (4 STEPS). THE SLIP FLAG IS SET, THE SLIP COUNTER IS
03900 01101                              * INCREMENTED, THE PLUNGER POSITION IS SET BACK TO 20 (ITS ASSUMED
03910 01102                              * POSITION, THE FINISH DELIVERY ROUTINE IS RE-ENABLED AND THE VALVE
03920 01103                              * OPENING ROUTINE IS SUSPENDED.
03930 01104                              * WHEN THIS ROUTINE IS CALLED A SECOND TIME, IF THE PLUNGER IS DOWN
03940 01105                              * THE SLIP FLAG WILL BE CLEARED.  IF THE PLUNGER IS STILL NOT DOWN, A
03950 01106                              * FAILURE MESSAGE WILL RESULT.

03970 01108A 14C6 07 28 08 14D1          BRCLR  PFLAG$,PFLAG,CON184 IF PLUNGER FLAG CLOSED,
03980 01109A 14C9 09 56 08 14D4          BRCLR  SLIP$,SLIP,CON187 IF SLIP FLAG SET,
03990 01110A 14CC A6 17         A        LDA    #PLNGFL
04000 01111A 14CE CD 170D       A        JSR    FAIL      SET FAILURE NUMBER
04010 01112A 14D1 19 56         A CON184 BCLR   SLIP$,SLIP CLEAR THE SLIP FLAG
04020 01113A 14D3 81                     RTS              RETURN
```

```
04040 01115                          * ROUTINE TO CATCH UP A SLIPPED PLUNGER MOTOR SECTOR
04050 01116A 14D4 13 2D   A CON187 BCLR   VLVOP$,CYCFLG DISABLE FURTHER VALVE OPENING
04060 01117A 14D6 10 2D   A        BSET   FIN$,CYCFLG RE-ENABLE FINISH DELIVERY ROUTINE
04070 01118A 14D8 A6 14   A        LDA    #20
04080 01119A 14DA B7 30   A        STA    PLUNGR    SET PLUNGER POSITION AT 20
04090 01120A 14DC AD 01  14DF      BSR    MTRSLP    SET SLIP FLAG AND INCREMENT SLIP COUNTER
04100 01121A 14DE 81                RTS
04120 01123          14DF  A MTRSLP EQU    *
04130 01124                          * SUBROUTINE MOTOR SLIP SETS THE SLIP FLAG, INCREMENTS THE SLIP COUNTER
04140 01125                          * AND TESTS THAT THE SLIP COUNTER IS LESS THAN 3. THE SLIP COUNTER IS
04150 01126                          * CLEARED EVERY 10 PUMP CYCLES IN SUBROUTINE CYCCMP.
04160 01127A 14DF 18 56   A        BSET   SLIP$,SLIP SET THE SLIP FLAG
04170 01128A 14E1 3C 3B   A        INC    SLPCTR    INCREMENT THE SLIP COUNTER
04180 01129A 14E3 B6 3B   A        LDA    SLPCTR    COMPARE SLIP COUNTER
04190 01130A 14E5 A1 03   A        CMP    #3        WITH 3
04200 01131A 14E7 25 05  14EE      BLO    RTRN15    IF GREATER THAN OR EQUAL
04210 01132A 14E9 A6 18   A        LDA    #MTRFL    SET THE FAILURE NUMBER
04220 01133A 14EB CD 170D A        JSR    FAIL
04230 01134A 14EE 81                RTRN15 RTS
04250 01136          14EF  A MPOWER EQU    *
04260 01137                          * SUBROUTINE MPOWER CONVERTS THE CHANGING MOTOR POSITIONS TO THE REQUIRED
04270 01138                          * PHASING AND ALSO CONTROLS THE SWITCHING TO LOWER HOLD CURRENTS AS
04280 01139                          * APPROPRIATE IN ORDER TO SAVE POWER 04300 01141                          * ROUTINE TO CONVERT PLUNGER POSITION TO REQUIRED MOTOR PHASING
04310 01142A 14EF B6 30   A        LDA    PLUNGR    LOAD A REGISTER WITH PLUNGER POSITION
04320 01143A 14F1 B1 31   A        CMP    LPLNGR    COMPARE WITH LAST PLUNGER POSITION
04330 01144A 14F3 27 04  14F9      BEQ    CON190    IF NOT EQUAL,
04340 01145A 14F5 3F 32   A        CLR    PPTMR     CLEAR PLUNGER POWER TIMER
04350 01146A 14F7 B7 31   A        STA    LPLNGR    UPDATE LAST PLUNGER POSITION
04360 01147A 14F9 AB 00   A CON190 ADD    #0        ALTER MOTOR PHASING
04370 01148A 14FB AD 35  1532      BSR    BINSTP    CONVERT POSITION TO STEPPING MOTOR CODE
04380 01149A 14FD 3C 32   A        INC    PPTMR     INCREMENT PLUNGER POWER TIMER
04390 01150A 14FF AE 03   A        LDX    #3        COMPARE PLUNGER POWER TIMER
04400 01151A 1501 B3 32   A        CPX    PPTMR     WITH 3
04410 01152A 1503 22 06  150B      BHI    CON193    IF GREATER THAN OR EQUAL TO,
04420 01153A 1505 BF 32   A        STX    PPTMR     RESET PLUNGER POWER TIMER TO 3
04430 01154A 1507 48              LSLA              SHIFT STEPPING MOTOR CODE
04440 01155A 1508 48              LSLA              FROM MOTOR STEPPING DRIVERS
04450 01156A 1509 48              LSLA              TO MOTOR HOLDING DRIVERS
04460 01157A 150A 48              LSLA
04470 01158A 150B B7 21   A CON193 STA   PPHASE    STORE CALCULATED PLUNGER MOTOR PHASING 04490 01160                          * ROUTINE TO CONVERT VALVE POSITION TO REQUIRED MOTOR PHASING
04500 01161A 150D B6 33   A        LDA    VALVE     LOAD A REGISTER WITH VALVE POSITION
04510 01162A 150F B1 34   A        CMP    LVALVE    COMPARE WITH LAST VALVE POSITION
04520 01163A 1511 27 04  1517      BEQ    CON196    IF NOT EQUAL,
04530 01164A 1513 3F 35   A        CLR    VPTMR     CLEAR VALVE POWER TIMER
04540 01165A 1515 B7 34   A        STA    LVALVE    UPDATE LAST VALVE POSITION
04550 01166A 1517 43              CON196 COMA      REVERSE MOTOR DIRECTION
04560 01167A 1518 AB 00   A        ADD    #0        ALTER MOTOR PHASING
04570 01168A 151A AD 16  1532      BSR    BINSTP    CONVERT POSITION TO STEPPING MOTOR CODE
04580 01169A 151C 3C 35   A        INC    VPTMR     INCREMENT VALVE POWER TIMER
04590 01170A 151E AE 03   A        LDX    #3        COMPARE VALVE POWER TIMER
04600 01171A 1520 B3 35   A        CPX    VPTMR     WITH 3
04610 01172A 1522 22 0B  152F      BHI    CON200    IF GREATER THAN OR EQUAL TO,
04620 01173A 1524 BF 35   A        STX    VPTMR     RESET VALVE POWER TIMER TO 3
04630 01174A 1526 48              LSLA              SHIFT STEPPING MOTOR CODE
04640 01175A 1527 48              LSLA              FROM MOTOR STEPPING DRIVERS
04650 01176A 1528 48              LSLA              TO MOTOR HOLDING DRIVERS
04660 01177A 1529 48              LSLA
04670 01178A 152A 3D 33   A        TST    VALVE     TEST FOR VALVE AT POSITION 0
04680 01179A 152C 26 01  152F      BNE    CON200    IF TRUE,
04690 01180A 152E 4F              CLRA              TURN OFF ALL VALVE MOTOR DRIVERS
04700 01181A 152F B7 22   A CON200 STA   VPHASE    STORE CALCULATED VALVE MOTOR PHASING
04710 01182A 1531 81               RTS
04730 01184          1532  A BINSTP EQU    *
04740 01185                          * SUBROUTINE BINSTP CONVERTS A BINARY NUMBER TO ITS STEPPING MOTOR
04750 01186                          * CODE EQUIVALENT 04770 01188A 1532 A4 03   A        AND    #%00000011 STRIP ALL BUT 2 LSB OF POSITION
04780 01189A 1534 97              TAX
04790 01190A 1535 D6 1539  A        LDA    STPTBL,X  LOOK UP MOTOR PHASING IN STEP TABLE
04800 01191A 1538 81               RTS 04820 01193A 1539    0A   A STPTBL FCB    %1010
04830 01194A 153A    09   A        FCB    %1001
04840 01195A 153B    05   A        FCB    %0101
04850 01196A 153C    06   A        FCB    %0110
```

As indicated previously, the stepping motor control procedure of the present invention may, with suitable modification, be employed to operate the fluid metering device of co-pending application Ser. No. 174,666. Indeed, the major distinction between the fluid metering device illustrated in FIG. 2 and the fluid metering device of application Ser. No. 174,666 is the use in the latter device of a pressure actuated valve mechanism, as opposed to a cam and stepping motor actuated valve mechanism, for opening and closing the inlet port to the pumping chamber. Hence, the only substantial modification necessary to render the stepping motor control procedure of the present invention compatible with the fluid metering device of application Ser. No. 174,666 involves eliminating that portion of the stepping motor control procedure directed to the valve stepping motor operating sequences.

It is also to be understood that additional modifications to the stepping motor control procedure disclosed in FIGS. 4 through 9 may be made by those skilled in the art without departing from the spirit and scope of the present invention. All such modifications and variations are, of course, considered to be within the purview of the appended claims.

What is claimed is:

1. A method for precise metering of fluids from a metering device, the metering device including a pumping means for providing reciprocal motion to pump fluid from the metering device, a motor means which serves as a source of rotational movement and a camming means which converts the rotational movement of the motor means into the reciprocal motion of the pumping means by rotating with the motor means to move the pumping means through greater and lesser rectilinear displacements as a function of the angular displacement of the motor means, said method comprising the steps of:

operating the motor means at relatively faster rotational speeds during those periods when the camming means moves the pumping means through rectilinear displacements of lesser magnitude; and operating the motor means at relatively slower rotational speeds during those periods when the camming means moves the piston means through rectilinear displacements of greater magnitude.

2. The method as set forth in claim 1, wherein said motor means includes a stepping motor which operates in incremental steps to rotate the camming means through equal angular displacements, each angular displacement of the camming means producing a greater or lesser rectilinear displacement of the pumping means as a function of the total angular displacement of the motor means, said step of operating the motor means at said relatively faster rotational speeds including the further step of shifting the stepping motor through incremental steps at relatively shorter intervals during those periods when the angular displacements of the camming means produce lesser rectilinear displacements of the pumping means and said step of operating the motor means at said relatively slower rotational speeds includes the further step of shifting the stepping motor through incremental steps at relatively longer intervals during those periods when the angular displacements of the camming means produce greater rectilinear displacements of the pumping means.

3. A pump controller mechanism that drives a pump for metering intravenous fluids to a patient at a predetermined rate in a relatively continous, nonpulsatile fashion, said mechanism comprising a stepping motor, having a rotatable output shaft, a plunger for displacing fluid in a pumping chamber, rotatable camming means driven by the output shaft and operatively connected to the plunger for driving the plunger in incremental linear movements downwardly for expelling fluid from the chamber and upwardly for permitting the refilling of the chamber, said camming means being arranged to be driven through a plurality of incremental equiangular movements providing a linear output drive for the plunger wherein the incremental linear movements of the plunger at the beginning and end of the pumping stroke are substantially shorter in length than those during the rest of the stroke, said incremental movements in said rest of the stroke all being of generally the same length, and control means for driving said motor so that the camming means is driven at a high rate of speed through those equiangular movements which produce shorter incremental linear movements of the plunger just prior to the completion of its downward movement, during the upward movement of the plunger while the pumping chamber is refilled with fluid, and during the initial downward movement of the plunger and so that the camming means is driven at a lower rate of speed during the remainder of its movement so that the average rate of delivery from the pump over the entire pumping cycle generally equals the delivery rate provided by the lower rate of speed, said high rate of speed accommodating both the time required for refilling the chamber and the shorter incremental movements at the beginning and end of the pumping stroke.

4. A positive displacement intravenous administration pump controller comprising a stepping motor having an incrementally rotatable drive shaft, a plunger operatively connected to said driveshaft for displacing fluid in an intraveous administration pump in a manner such that the plunger is moved in one direction during a filling portion of the operating cycle and in the opposite direction during the pumping portion of the operating cycle, means for driving said drive shaft of the motor through a plurality of equiangular distances, and control circuitry for controlling the rate at which said driving means is operated, said control circuitry including means for operating said driving means at a predetermined high rate during the filling portion and a part of the pumping portion of the operating cycle, and means for operating said driving means at a second rate during the remainder of the pumping portion, said second rate causing the fluid to be delivered at a desired preset rate over the operating cycle, and means for controlling the time that the high rate is maintained during the pumping portion of the cycle so that the average rate over the entire operating cycle equals the desired preset rate, said last named means including a storing means, means for periodically updating the storing means throughout the operating cycle by an incremental value determined by the desired preset rate, means for comparing at the periodic rate the total value in the storing means during the pumping portion of the operating cycle with a second value equivalent to the amount of fluid to be delivered during one incremental movement of the drive shaft, and means for activating said motor to cause it to rotate the drive shaft through one of said equiangular distances when value in the storing means is equal to or greater than said second value.

* * * * *